(12) United States Patent
Yang et al.

(10) Patent No.: US 11,752,118 B2
(45) Date of Patent: *Sep. 12, 2023

(54) METHOD FOR TREATING MELANOMA (71) Applicant: GONGWIN BIOPHARM CO., LTD, Taipei (TW)

(72) Inventors: Chuan-Ching Yang, Taipei (TW); Mao-Yuan Lin, Taipei (TW); Shun-Chi Wu, Taipei (TW); Zong-Yu Yang, Taipei (TW); Di-Rong Chen, Taipei (TW); Chi-Chiang Tu, Taipei (TW); Nan-Shan Zhong, Guangzhou (CN)

(73) Assignee: GONGWIN BIOPHARM CO., LTD, Taipei (TW)

( * ) Notice: Subject to any disclaimer, the term of this patent is extended or adjusted under 35 U.S.C. 154(b) by 254 days.

This patent is subject to a terminal disclaimer.

(21) Appl. No.: 17/109,993

(22) Filed: Dec. 2, 2020

(65) Prior Publication Data
US 2022/0168248 A1 Jun. 2, 2022

(51) Int. Cl.
| | |
|---|---|
| *A61K 31/18* | (2006.01) |
| *A61K 47/34* | (2017.01) |
| *A61K 47/10* | (2017.01) |
| *A61K 47/12* | (2006.01) |
| *A61K 47/20* | (2006.01) |
| *A61P 35/00* | (2006.01) |
| *A61K 31/40* | (2006.01) |
| *A61K 31/397* | (2006.01) |
| *A61K 31/337* | (2006.01) |
| *A61K 31/495* | (2006.01) |
| *A61K 31/445* | (2006.01) |

(52) U.S. Cl.
CPC .......... *A61K 31/18* (2013.01); *A61K 31/337* (2013.01); *A61K 31/397* (2013.01); *A61K 31/40* (2013.01); *A61K 31/445* (2013.01); *A61K 31/495* (2013.01); *A61K 47/10* (2013.01); *A61K 47/12* (2013.01); *A61K 47/20* (2013.01); *A61K 47/34* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 10,485,773 B2 * | 11/2019 | Yang | ................... A61K 31/18 |
| 2003/0045755 A1 | 3/2003 | Burns | |
| 2017/0172951 A1 | 6/2017 | Yang et al. | |
| 2020/0338028 A1 | 10/2020 | Yang et al. | |

FOREIGN PATENT DOCUMENTS

| | | |
|---|---|---|
| KR | 10-2018-0005079 A | 1/2018 |
| WO | 2017-214619 A1 | 12/2017 |

OTHER PUBLICATIONS

Banerjee et al., Journal of Medicinal Chemistry (2017), 60(4), pp. 1309-1324.*
International Search Report Issued in Application No. PCT/US2021/058054, dated Feb. 18, 2022, 4 pages.
Written Opinion Issued in Application No. PCT/US2021/058054, dated Feb. 18, 2022, 4 pages.

* cited by examiner

*Primary Examiner* — Brian J Davis
(74) *Attorney, Agent, or Firm* — Osha Bergman Watanabe & Burton LLP (57) ABSTRACT

Provided is a pharmaceutical composition for treating melanoma, including a benzenesulfonamide derivative and a pharmaceutically acceptable carrier thereof. Also provided is a method for treating melanoma by administering the composition to a subject in need thereof. Further provided is a use of the pharmaceutical composition in the manufacture of a medicament for treating melanoma.

19 Claims, 2 Drawing Sheets

METHOD FOR TREATING MELANOMA

BACKGROUND

1. Technical Field

The present disclosure relates to methods for treating melanoma, and particularly to methods for treating non-UV-induced melanoma.

2. Description of Related Art

Melanoma represents a significant health problem with over 76,690 newly diagnosed cases and over 9,480 deaths annually in the United States alone (Howlader et al., 2013). Human malignant melanoma is a highly heterogeneous cancer that develops from melanocytes and occurs in numerous anatomical sites with different pathogenesis. The major subtypes of human malignant melanoma include UV-induced melanoma and non-UV-induced melanoma such as acral, mucosal, and ocular melanomas. Epidemiology, UV-radiation status, histopathological features, genetics, prognosis, and outcomes may vary considerably between these subtypes of melanomas.

Acral melanomas are usually located on the palms of the hands, soles of the feet, and the nail apparatus, which occur at similar incidences across all world populations (Tsao et al., Genes Dev. 26: 1131-1155, 2012). Among different subtypes, acral melanomas carry a poor prognosis as compared with other melanomas (Greenwald et al., Melanoma Res. 22: 1-8, 2012).

Mucosal melanomas originate from melanocytes within mucosal epithelia. They usually occur in anogenital regions, oropharynx and paranasal sinuses, as well as conjunctiva (head and neck localizations), and can also arise from parotid glands, oesophagus, and the middle ear (Marcus et al., J. Skin Cancer 2012, 231693, 2012). Local and/or distant metastasis to lungs and liver occur in 50% of cases with head and neck melanoma, and mucosal melanomas carry a poor prognosis, with a 5-year survival rate between 25% and 33% (Williams, Head Neck Pathol. 11: 110-117, 2017).

Uveal melanoma is the most common intraocular human cancer and accounts for approximately 5% of all melanoma in the United States. Also, uveal melanoma is lethal. Almost half of the patients with effective primary therapy will develop metastases, and these patients usually have a poor prognosis, with a median survival time (MST) ranging from 4 to 15 months (Robertson et al., Cancer Cell 33: 151.17, 2018).

Melanomas are quite common in the dogs and cats, and most of them are malignant (Brockley et al., N. Z. Vet. J. 61: 25-31, 2013). The melanomas of dogs or cats usually occur in the oral cavity. In addition, the melanomas also occur in the haired skin, nail bed, footpad, eye, gastro-intestinal tract, central nervous system, or muco-cutaneous junction. Oral melanomas present the worse prognosis with a median survival time of 6 months, and digital melanomas have intermediate prognosis with an MST of 11.8 months.

Oral melanoma and digital melanoma in dogs and cats are quite malignant tumors with a high tendency of local invasion and metastasis. The current treatment is based on surgical resection. However, for oral melanoma originating from the gums or very close to the bone, partial mandibular or upper jaw resection is usually required to achieve complete resection. Moreover, surgical removal of digital melanoma requires partial or full amputation. Radiation therapy alone or combined with chemotherapy can also be used to treat oral melanoma in dogs or cats. However, the local recurrence rate may be as high as 45%, and side effects such as mucosal hyperemia, mucositis, ulcers, and bleeding may occur. Therefore, such surgical resection or radiation therapy may seriously affect the quality of life of the dogs and cats.

Up to now, there is still lack of effective and safe pharmaceutical compositions for treating non-UV-induced melanoma of humans and oral and digital melanoma of dogs and cats. As malignant melanoma seriously threatens the health of humans and non-human mammals, e.g., dogs and cats, it is an urgent unmet need to develop pharmaceutical compositions that can break through the current technical limitation and solve problems in this field.

SUMMARY

In view of the above-mentioned problems in the technical field, the present disclosure provides effective and safe pharmaceutical compositions that can be used for the treatment or adjuvant treatment of melanoma. Interventional therapy by the present disclosure can effectively avoid amputation in the case of inoperable conditions and improve the overall quality of life of patients or animals suffering from melanoma.

The present disclosure provides a pharmaceutical composition for treating melanoma. The pharmaceutical composition comprises a benzenesulfonamide derivative and a pharmaceutically acceptable carrier thereof.

In at least one embodiment of the present disclosure, the benzenesulfonamide derivative is represented by formula (I) below:

or a pharmaceutically acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring.

In at least one embodiment of the present disclosure, the alkyl, alkoxy, cycloalkyl, cycloheteroalkyl groups and the ring in $R_1$ to $R_7$ are independently unsubstituted or substituted with one or more substituents. In some embodiments of the present disclosure, the substituent is selected from the group consisting of phenyl, halo, oxo, ether, hydroxyl, carboxyl, amino, sulfo and sulfonamide group.

In at least one embodiment of the present disclosure, the benzenesulfonamide derivative or the pharmaceutically acceptable salt thereof may be at least one selected from the group consisting of para-toluene sulfonamide (p-TSA), ortho-toluene sulfonamide, meta-toluene sulfonamide, N-ethyl-ortho-toluene sulfonamide, N-ethyl-para-toluene sulfonamide, N-cyclohexyl-para-toluene sulfonamide, The present disclosure also provides a method for treating melanoma, comprising administering an effective amount of the pharmaceutical composition of the present disclosure to a subject in need thereof.

In at least one embodiment of the present disclosure, the pharmaceutical composition causes ablation of melanoma.

In at least one embodiment of the present disclosure, the melanoma is non-UV-induced melanoma.

In at least one embodiment of the present disclosure, the subject is a human, a dog, or a cat.

DETAILED DESCRIPTION

The following examples are used to exemplify the present disclosure. A person of ordinary skill in the art can understand the other advantages of the present disclosure, based on the specification of the present disclosure. The present disclosure can also be implemented or applied as described in different examples. It is possible to modify and/or alter the above examples for carrying out this disclosure without contravening its scope for different aspects and applications.

It is noted that, as used in this specification, the singular forms "a," "an," and "the" include plural referents unless expressly and unequivocally limited to one referent. The term "or" is used interchangeably with the term "and/or" unless the context clearly indicates otherwise.

The present disclosure provides a pharmaceutical composition for treating melanoma, comprising a benzenesulfonamide derivative and a pharmaceutically acceptable carrier thereof.

In at least one embodiment of the present disclosure, the benzenesulfonamide derivative is represented by formula (I):

or a pharmaceutically or acceptable salt thereof, wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring.

In at least one embodiment of the present disclosure, the alkyl, alkoxy, cycloalkyl, cycloheteroalkyl groups and the ring in $R_1$ to $R_7$ are independently unsubstituted or substituted with one or more substituents. In some embodiments of the present disclosure, the substituent is selected from the group consisting of phenyl, halo, oxo, ether, hydroxyl, carboxyl, amino, sulfo and sulfonamide group.

In at least one embodiment of the present disclosure, the benzenesulfonamide derivative or the pharmaceutically acceptable salt thereof may be at least one selected from the group consisting of para-toluene sulfonamide (p-TSA), ortho-toluene sulfonamide, meta-toluene sulfonamide, N-ethyl-ortho-toluene sulfonamide, N-ethyl-para-toluene sulfonamide, N-cyclohexyl-para-toluene sulfonamide, In at least one embodiment of the present disclosure, the pharmaceutically acceptable carrier may be a filler, a binder, a preservative, a disintegrating agent, a lubricant, a suspending agent, a wetting agent, a flavoring agent, a thickening agent, an acid, a biocompatible solvent, a surfactant, a complexation agent, or any combination thereof.

In at least one embodiment of the present disclosure, the binder may be paste, sorbitol, guar gum, polyvinylpyrrolidone, cellulose derivatives such as hydroxypropyl methylcellulose, carboxymethyl cellulose, carbomer (commercially available as Carbopols), or any combination thereof.

In at least one embodiment of the present disclosure, the preservative may be sodium benzoate, methyl paraben, propyl paraben, cresol, or any combination thereof.

In at least one embodiment of the present disclosure, the lubricant may be metal stearates (such as magnesium stearate, calcium stearate, or sodium stearate), stearic acid, talc, polyethylene glycol, soluble salts (such as sodium chloride or sodium benzoate), or any combination thereof.

In at least one embodiment of the present disclosure, the flavoring agent may be peppermint oil, menthol, lemon oil, orange oil, cinnamon oil, or any combination thereof.

In at least one embodiment of the present disclosure, the pharmaceutically acceptable carrier may be polyethylene glycol (PEG), alkylene glycol, propylene glycol, sebacic acid, dimethyl sulfoxide (DMSO), ethanol, or any combination thereof. The examples of the alkylene glycol include, but are not limited to, 2-ethyl-1,3-hexanediol and propanediol. The example of the PEG includes, but is not limited to, PEG-400.

In at least one embodiment of the present disclosure, the benzenesulfonamide derivative is in an amount of 1% to 60% of the composition by weight. For example, an amount of the benzenesulfonamide derivative in the composition has a lower limit chosen from 1%, 5%, 10%, 15%, 20%, and 25% of the composition by weight, and an upper limit chosen from 60%, 55%, 50%, 45%, 40%, and 35% of the composition by weight.

In at least one embodiment of the present disclosure, the pharmaceutically acceptable carrier is in an amount of 25% to 99% of the composition by weight. For example, an amount of the pharmaceutically acceptable carrier in the composition has a lower limit chosen from 25%, 30%, 35%, and 40% of the composition by weight, and an upper limit chosen from 99%, 95%, 90%, 80%, 70%, and 60% of the composition by weight.

In at least one embodiment of the present disclosure, the pharmaceutically acceptable carrier is chosen from at least one of 10% to 40% by weight of PEG, 5% to 10% by weight of propylene glycol, 1% to 5% by weight of sebacic acid, 0% to 15% by weight of p-toluenesulfonic acid, 10% to 20% by weight of 2-ethyl-1,3-hexanediol, 0% to 10% by weight of DMSO, and 0% to 20% by weight of ethanol.

In at least one embodiment of the present disclosure, the pharmaceutical composition may be formulated into a form suitable for parenteral administration, injection, continuous perfusion, sublingual administration, subcutaneous administration, topical administration, or oral administration. For example, the pharmaceutical composition may be, but is not limited to, a formulation to injection, dry powder, a tablet, an oral liquid, a wafer, a film, a lozenge, a capsule, a granule, a pill, a gel, a lotion, an ointment, an emulsifier, a paste, a cream, an eye drop, or a salve.

The present disclosure also provides a method for treating melanoma, comprising administering a therapeutically effective amount of the pharmaceutical composition of the present disclosure to a subject in need thereof.

As used herein, the term "melanoma" refers to any malignant form of cancer that arises from melanocytes. For example, the melanoma may include, but is not limited to, mucosal melanoma, acral melanoma, ocular melanoma, cutaneous melanoma, superficial spreading melanoma, nodular melanoma, polypoid melanoma, lentigo maligna melanoma, desmoplastic melanoma, soft-tissue melanoma, amelanotic melanoma, juvenile melanoma, Harding-Passey melanoma, subungual melanoma, spitzoid melanoma, blue nevus-like melanoma, or any combination thereof. The melanoma may also include, but is not limited to, metastatic melanoma. Ultraviolet (UV) radiation status, epidemiology, histopathological features, genetics, prognosis, and outcomes may be different between these subtypes of melanomas.

In at least one embodiment of the present disclosure, the melanoma is non-UV-induced melanoma. The non-UV-induced melanoma includes, but is not limited to, mucosal melanoma, acral melanoma, ocular melanoma, non-UV-induced cutaneous melanoma, or any combination thereof. The mucosal melanoma may appear in, but is not limited to, oral cavity, gingiva, nasal cavity, paranasal sinuses, respiratory tract, digestive tract, urinary tract, transitional region of anal canal, genitourinary tract, vagina, or vulva. The acral melanomas may appear in, but is not limited to, a finger, a toe, a digit, a palm, a paw, a sole, a nail, or a nail fold. The ocular melanoma may appear in, but is not limited to, cornea, uvea, or conjunctiva.

In at least one embodiment of the present disclosure, the subject may be a human or a non-human mammal such as a dog, a cat, a horse, a mouse, a rat, a primate, a pig, a sheep, a goat, an antelope, an alpaca, a llama, a cow, a buffalo, a bison, a donkey, a mule, a deer, an elk, or a camel. For example, the method may effectively treat a human suffering from mucosal melanoma, acral melanoma, uveal melanoma, or any combination thereof. For other examples, the method may effectively treat a dog or a cat suffering from oral mucosal melanoma, digital melanoma, uveal melanoma, or any combination thereof.

In at least one embodiment of the present disclosure, the pharmaceutical composition may be administered to the subject intratumorally, intravenously, subcutaneously, intradermally, orally, intrathecally, intraperitoneally, intranasally, intramuscularly, intrapleuraly, topically, or through nebulization.

In at least one embodiment of the present disclosure, the benzenesulfonamide derivative in the pharmaceutical composition may be administered to the subject in a therapeutically effective amount of from about 100 mg to about 26,400 mg during a treatment period or a treatment cycle, such as 132 mg to 3,300 mg, 300 mg to 7,000 mg or 3,300 mg to 26,400 mg. As used herein, the term "treatment cycle" refers to a treatment period followed by a rest period without treatment that is repeated on a regular schedule.

In some embodiments of the present disclosure, the injection dosage for treating melanoma may be in a range of from about 100 mg to about 7,000 mg, such as 165 mg to 6,600 mg, 300 mg to 7,000 mg, 330 mg to 6,600 mg, 495 mg to 3,300 mg, and 660 mg to 1,650 mg of p-toluenesulfonamide or other benzenesulfonamide derivatives.

In at least one embodiment of the present disclosure, the pharmaceutical composition can be used to treat melanoma, e.g., non-UV-induced melanoma by triggering the ablation of melanoma. In at least one embodiment of the present disclosure, the dosage of intratumoral injection for the ablation of melanoma is 0.4 mL to 10 mL (about 132 mg to 3,300 mg of p-toluenesulfonamide or other benzenesulfonamide derivatives).

In at least one embodiment of the present disclosure, the pharmaceutical composition may be administered to the subject 1 to 4 times per day, 1 to 4 times per week, or 1 to 4 times per month. In at least one embodiment of the present disclosure, the composition may be administered to the subject for a 1- to 4-week or 1- to 4-month treatment period or treatment cycle. In some embodiments of the present disclosure, the composition may be administered to the subject 2 to 3 times per week for a 2-week treatment period. In at least one embodiment of the present disclosure, the composition is administered to the subject equal to or more than 4 times in the first treatment period.

In at least one embodiment of the present disclosure, the pharmaceutical composition can be directly injected into melanoma or injected into the area surrounding the melanoma. In some embodiments of the present disclosure, the dosage can be proportionally increased or decreased according to a therapeutic situation. In at least one embodiment of the present disclosure, the administration may continue until the melanoma shrinks 5%, 10%, 15%, 20%, 25%, 30%, 35%, 40%, 45%, 50%, 55%, 60%, 65%, 70%, 75%, 80%, 85%, 90%, or 95% (by volume or weight), or until the melanoma is fully eliminated.

The present disclosure also provides a use of a pharmaceutical composition in the manufacture of a medicament for treating melanoma, wherein the pharmaceutical composition comprises a benzenesulfonamide derivative of the present disclosure and a pharmaceutically acceptable carrier thereof.

The following are embodiments further demonstrating the efficacy of the current disclosure, but not to limit the scope of the present disclosure.

EXAMPLES

The present disclosure is further described by means of the following examples. However, these examples are only illustrative of the disclosure, and in no way limit the scope and meaning of the present disclosure. Indeed, many modifications and variations of the present disclosure will be apparent to those skilled in the art upon reading this specification, and can be made without departing from its scope.

Preparation Example

Pharmaceutical Composition of Benzenesulfonamides (GWM100):

| | |
|---|---|
| p-Toluenesulfonamide | 1%-60% |
| PEG-400 | 10%-40% |
| 1,2-Propylene glycol | 5%-10% |
| Sebacic acid | 1%-5% |
| p-Toluenesulfonic acid | 0%-15% |
| 2-Ethyl-1,3-hexanediol | 10%-20% |
| Dimethyl sulfoxide | 0-10% |
| Ethanol | 0-20% |

Preparation of the composition of the present disclosure includes the process of: adding and mixing the solvents and adjuvants in a given ratio; heating the mixture to 80° C. to 110° C. with stirring to form a clear oily liquid; gradually adding the sulfa drug with stirring until completely dissolved; filtering and cooling the mixture to obtain the composition of the present disclosure in an oily liquid form (GWM100).

The preparation of the GWM100 injection may be conducted by some techniques known in the art, e.g., adding an adjuvant and/or solvent to adjust the mixture to an isotonic state, or filtering the mixture by using a microporous filter.

The present disclosure also provides the use of GWM100 as a medicament for treating melanoma, e.g., non-UV-induced melanoma. In at least one embodiment of the present disclosure, GWM100 can be used to treat melanoma by triggering the ablation of melanoma.

It is confirmed by clinical trials that the pharmaceutical composition of the present disclosure can effectively treat melanoma, e.g., non-UV-induced melanoma, in human, dog, or cat. The efficacy of melanoma treatment provided in the present disclosure was assessed by the following clinical trials.

Embodiment 1

The clinical trials were conducted at Peking University Hospital of Stomatology, Tianjin Medical University Cancer Hospital, and Liaoning Cancer Hospital from January 2006 to December 2006. The trial enrolled 3 patients diagnosed as melanoma by pathology, including 1 man and 2 women aged between 25 and 50, with an average age of 39. The trials followed the Helsinki Declaration (1996) and the relevant ethical principles of Good Clinical Practice, and were conducted according to the relevant regulations of the State Food and Drug Administration (SFDA). The trials were performed after approval by the ethics committee.

Mode of Administration

GWM100 was administered to the patients by intratumor injection via percutaneous puncture. All patients must undergo outpatient surgery for GWM100 treatment. For each injection, the patient's vital function was monitored during the treatment, and the vital signs check were confirmed after the surgery.

As to the method of administration, 5 mL (1,650 mg of p-toluenesulfonamide) of GWM100 was sucked from a glass ampoule and then slowly injected into the tumor by a puncture needle. The treatment period of GWM100 was 2 weeks, and the injection dose thereof was 2 to 3 doses per week. The first treatment period includes 4 or more treatments.

Depending on the size of the tumor, the maximum dose was 5 mL (1,650 mg of p-toluenesulfonamide) of GWM100. The maximum cumulative dose of GWM100 in one day was 10 mL (3,300 mg of p-toluenesulfonamide). It should be noted that the number of injections may depend on the range of necrotic tumors in its entirety.

Research Design

Open-label trails, single-arm trials, and non-random assignment research.

Research Results

The research recruited 3 patients and was completed based on full analysis set (FAS) and per protocol set (PPS). In these 3 cases, 66.7% (two cases) were oral melanoma, and 33.3% (one case) was cutaneous melanoma. Among these FAS patients, 66.7% were stage IV, and 33.3% was stage II. The primary endpoint for evaluating efficacy was based on the objective response rate of the target tumor according to the Response Evaluation Criteria in Solid Tumors (RECIST), and the assessment was conducted on the 7th day after the last dose (End Visit) and on the 30th day after the End Visit (Follow-up Visit). Tables 1 and 2 below summarize the therapeutic indexes of FAS and PPS.

TABLE 1

Summary of clinical trails

| Subject's ID | Location | Tumor Stage | RECIST response |
|---|---|---|---|
| 07105 | Oral | IV | PR |
| 16108 | Oral | II | SD |
| 18112 | Dermal | IV | PD |

CR: Complete Response; PR: Partial Response; SD: Stable Disease; PD: Progress Disease

TABLE 2

Summary of melanoma treatment in three cases

| Diagnosis | Case No. | CR | PR | SD | PD |
|---|---|---|---|---|---|
| Melanoma of the oral cavity | 2 | 0 | 1 | 1 | 0 |
| Melanoma of the cutaneous | 1 | 0 | 0 | 0 | 1 |
| Total | 3 | 0 | 1 | 1 | 1 |

CR: Complete Response; PR: Partial Response; SD: Stable Disease; PD: Progress Disease Three patients with melanoma were treated by intratumoral injection of GWM100. Patients No. 07105 and No.

16108 were diagnosed with oral mucosal melanoma that belongs to non-UV-induced melanoma. After a two-week treatment period, the tumor tissues of Patients No. 07105 and No. 16108 were significantly necrotic, and the condition of these two patients was improved. By contrast, Patient No. 18112 was pathologically diagnosed with UV-induced cutaneous melanoma that most commonly occurs on the scalp; however, the patient's condition had not improved after the two-week treatment period.

Therefore, the clinical trials demonstrate the superior therapeutic effect of GWM100 on non-UV-induced melanoma such as mucosal melanoma, acral melanoma, and ocular melanoma in humans.

Embodiment 2

The clinical trial of the treatment of melanoma in pet dogs and cats by GWM100 was carried out at Evergreen animal hospital in Taipei, Taiwan from January to August 2020.

Subject animals: Dog and cat

Diagnosis: Melanoma

The inclusion criteria are: (A) the subject is greater than or equal to 1 year old; (B) the subject is diagnosed with melanoma by cytology or histopathology; (C) the trial veterinarian assesses that the subject is unsuitable for removal of the melanoma by surgery; (D) the subject has at least one measurable lesion that is larger than 1 cm in diameter; (E) the trial veterinarian assesses the life expectancy of the subject to exceed 3 months; and (F) the owner can understand and abide by the experimental procedure and is willing to sign an informed consent form.

The exclusion criteria are: (A) the subject has received systemic chemotherapy within 4 weeks before entering the trial; (B) the subject has received radiotherapy within 4 weeks before entering the trial; (C) the subject has underwent a major operation (for example, thoracotomy is not allowed, but the non-invasive operation, such as biopsy, is allowed) within 4 weeks before entering the trial; (D) the subject is treated by any other experimental drugs, biological formulations, medical materials, or other anti-tumor treatments (such as immunomodulators and radiotherapy) within 4 weeks before entering this trial or during the period of this trial experiment; (E) the subject has the following abnormal value of blood tests before entering the trial: a. hemoglobin<6.0 g/dL; b. absolute neutrophil count (ANC) <1,500/µL; c. albumin<1.5 g/dL; d. total bilirubin<2 mg/dL; e. alanine aminotransferase (ALT) and aspartate aminotransferase (AST)>5× upper normal limit (UNL); f. International Renal Interest Society (IRIS) stage of chronic kidney disease (CKD)>stage 3; (F) the subject suffers from any other serious diseases such as infection, uncontrolled diabetes, stage C of chronic degenerative valve disease (CDVD, one of the heart diseases), gastric ulcer, severe autoimmune disease, and the trial veterinarian restricts the subject from participating in this trial after assessment; (G) the subject is known or suspected of having allergic reactions to the ingredients contained in any p-toluenesulfonamide drugs; (H) the trial veterinarian diagnoses that the subject's lesion was blocked by important blood vessels, so it is difficult to perform intratumoral injection therein; (I) the subject is pregnant; and (J) the trial veterinarian determines that the subject is unsuitable for participating in this trial.

Those who met at least one of the following criteria should be withdrawn from clinical trials: (A) the informed consent form is withdrawn; (B) the subject receives the treatment prohibited by this trial; (C) after assessing any pathological characteristics, clinical adverse events, or any changes in the condition of the subject, the trial veterinarian determines that it is not the most advantageous situation to allow the subject to continue participating in the trial; (D) the subject is pregnant during the treatment period or is suspected of being pregnant by its owner or the trial veterinarian; (E) the subject has an adverse event of grade 3 or above according to international adverse events of oncology organization (Veterinary Cooperative Oncology Group-Common Terminology Criteria for Adverse Events, VCOG-CTCAE) and cannot return to grade 1 within 7 days after the adverse event, or the grade 3 or above adverse event still occurs after 2 dose reductions in the subject; (F) signs and symptoms of disease progression or deterioration (assessment of deterioration was based on Veterinary Cooperative Oncology Group-Response Evaluation Criteria in Solid Tumours v1.0 (VCOG-RECIST v1.0)); (G) death; (H) loss of follow-up tracking; and (I) violation of the plan.

Treatment Method

The test pet was given intratumoral injections of the GWM100 drug on Day 1, 3, 5, 7, 11, 13, and 15 (about 330 to 990 mg of p-toluenesulfonamide each time). The injections were carried out in single, multi-point (4 to 5 points) intratumoral injections.

Response Assessment Criteria

The electronic vernier caliper measurement was performed before each administration, and the computed tomography (CT) scan was performed before the first administration and at the conclusion visit. Complete response (CR) means that a measurable or evaluable lesion disappears completely, and no new lesions appear for more than four weeks. Partial response (PR) means that a measurable or evaluable lesion shrinks by more than or equal to 30%, and no new lesions appear for more than four weeks. Stable disease (SD) means that a measurable or evaluable lesion shrinks by less than or equal to 30% or enlarges by less than or equal to 20%. Disease progression (PD) means that a measurable or evaluable lesion enlarges by more than or equal to 20%, or other lesions deteriorate, and new lesions appear.

Safety Assessment

When conducting safety assessment during the trial period, the relevant researchers of the trial were responsible for defining and compiling the adverse events in the protocol (the method for assessment was referred to "Veterinary Cooperative Oncology Group-Common Terminology Criteria for Adverse Events (VCOG-CTCAE)."

The followings show the treatment results of melanoma in Embodiment 2.

Case No. D01-S01-E01:

Case No. D01-S01-E01 is a 3-year-old female mongrel dog. Before administration, the heart function of the dog was normal. The dog had suffered from demodicosis, and the dog was observed with swollen lymph nodes on the posterior side of the left leg, which was suspected to be signs of metastasis. The lesion was located on the left hind paw of the dog and was diagnosed as melanoma (melanocytic tumors of uncertain malignant potential) according to the pathological section. The blood biochemical test report showed that the function of the dog's liver and kidney is normal.

Figure 1:
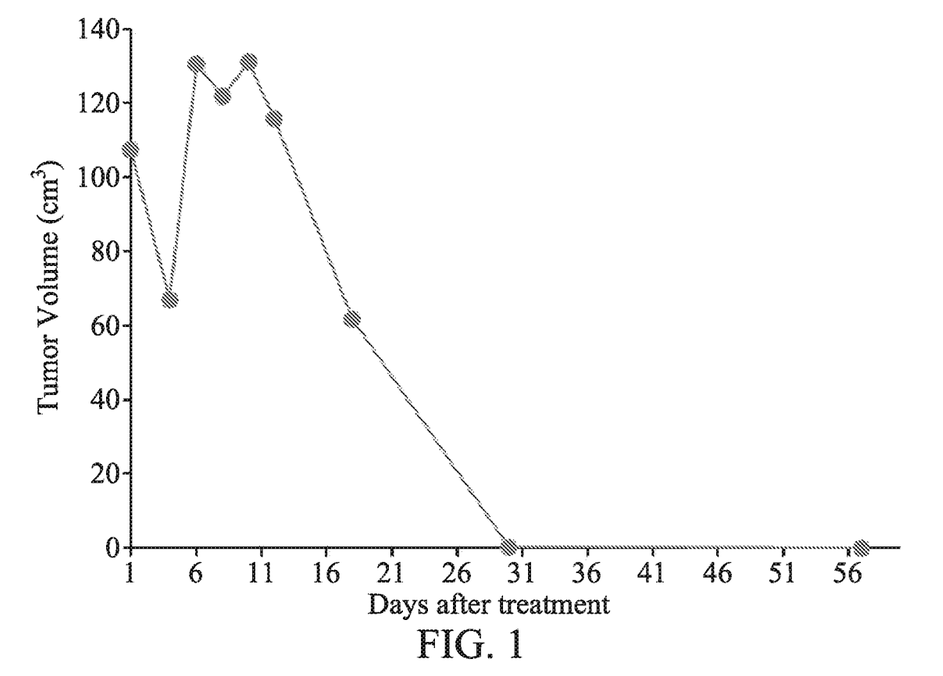
FIG. 1 shows the volume change of melanoma in the lesion of the dog (Case No. D01-S01-E01) treated with the GWM100 drug.

The target lesion was administered by seven intratumoral injections, and the tumor volume of the lesion was 108 cm$^3$ before the treatment (Day 1). After the seventh administration (Day 30), the tumor volume thereof was reduced to 0 cm$^3$ which could no longer be measured (referring to FIG. 1). According to the statistical results from data measured by the electronic vernier caliper during the treatment period, the size and volume of the tumor decreased significantly over time. The response rate of the target lesion was assessed by the veterinarian as complete response (CR), and the size of the target tumor reduced by 100%.

Therefore, administration of the GWM100 drug of the present disclosure could effectively reduce the tumor volume of digital melanoma by 100% in dogs.

Case No. D01-S02-E02:

Case No. D01-S02-E02 is a 16-year-old female mongrel dog. Before administration, the dog had slight insufficiency of cardiac function, while contractility of the heart was still within the normal range. In addition, the dog had abnormal renal function and gastrointestinal function and lymph node calcification due to immunotherapy. The dog also suffered from deformable spondylosis. The lesion was located in the left lower jaw of the dog's mouth and was a recurrent tumor, and the lesion was diagnosed as melanoma according to the pathological section. The blood biochemical test report showed that the dog had chronic liver disease, and kidney function thereof was normal.

Figure 2:
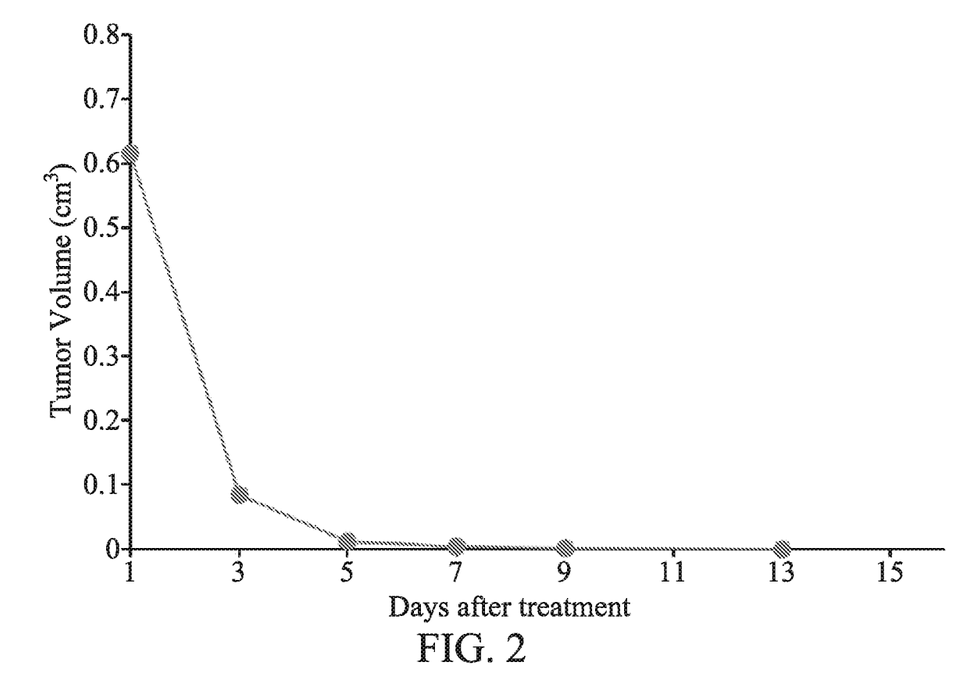
FIG. 2 shows the volume change of melanoma in the lesion of the dog (Case No. D01-S02-E02) treated with the GWM100 drug.

The target lesion was administered by five intratumoral injections, and the tumor volume of the lesion was 0.62 cm$^3$ before the treatment (Day 1). After the fifth administration (Day 9), the tumor volume thereof was reduced to 0 cm$^3$ which could no longer be measured (referring to FIG. 2). According to the statistical results from data measured by the electronic vernier caliper during the treatment period, the size and volume of the tumor decreased significantly over time. The response rate of the target lesion was assessed by the veterinarian as complete response (CR), and the size of the target tumor reduced by 100%.

Therefore, administration of the GWM100 drug of the present disclosure could effectively reduce the tumor volume of oral melanoma by 100% in dogs.

Case No. D01-S04-E04:

Case No. D01-S04-E04 is a 12-year-old female dog with a history of indolent lymphoma and hypertension. A pathology report showed that the dog suffered from melanoma inside the third toe of the hind limb. After consultation and a screening examination, the dog met the inclusion criteria. The blood biochemical test report showed that the values of liver and kidney function of the dog were all within the reference values.

Figure 3:
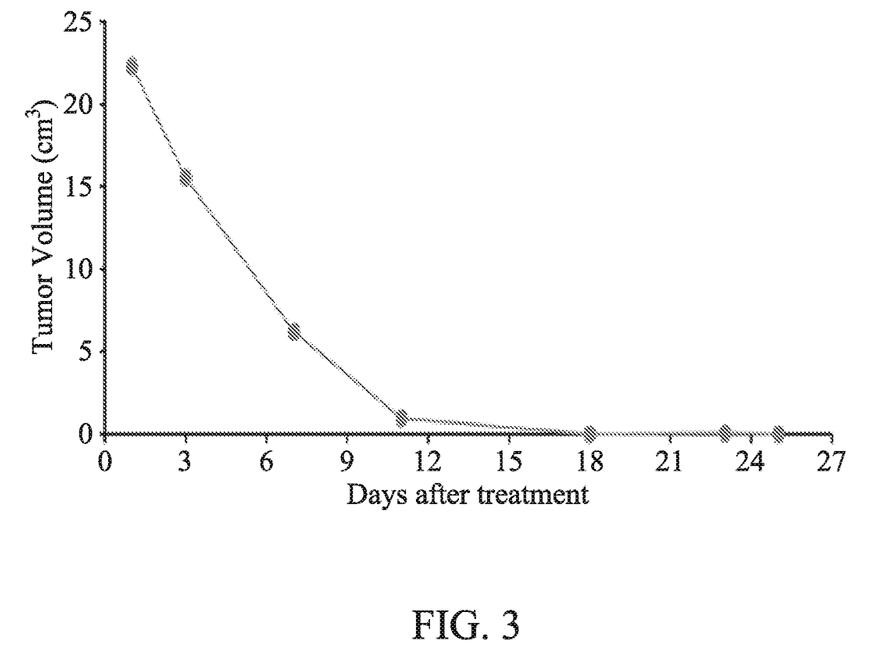
FIG. 3 shows the volume change of melanoma in the lesion of the dog (Case No. D01-S04-E04) treated with the GWM100 drug.

The tumor volume of the lesion was measured as 22 cm$^3$ before the treatment (Day 1), and the tumor volume thereof was reduced to 1 cm$^3$ after the fourth administration. After the fifth administration (Day 18), the tumor volume thereof was reduced to 0 cm$^3$ which could no longer be measured (referring to FIG. 3). The total number of administrations in the treatment period was seven. At the final evaluation visit (Day 25), the biochemical examination of serum showed that the values of liver and kidney function of the dog were all within the reference values. The response rate of the target lesion was complete response (CR), and the size of the target tumor reduced by 100%. The use of the GWM100 test drug of the present disclosure could reduce the tumor volume of melanoma by 100%.

Therefore, administration of the GWM100 drug of the present disclosure could effectively reduce the tumor volume of digital melanoma by 100% in dogs.

Case No. C01-S01-E01:

Case No. C01-S01-E01 is a 14-year-old male cat with a history of diabetes and pancreatitis. A pathological report showed that the cat suffered from melanoma on the metacarpal pad of the hind paw. After the blood glucose of cat was stabilized, consultation and a screening examination was performed. The biochemical examination of serum showed that the value of liver function of the cat fell within the reference values, and the renal function thereof was stable. Accordingly, the cat met the inclusion criteria.

Figure 4:
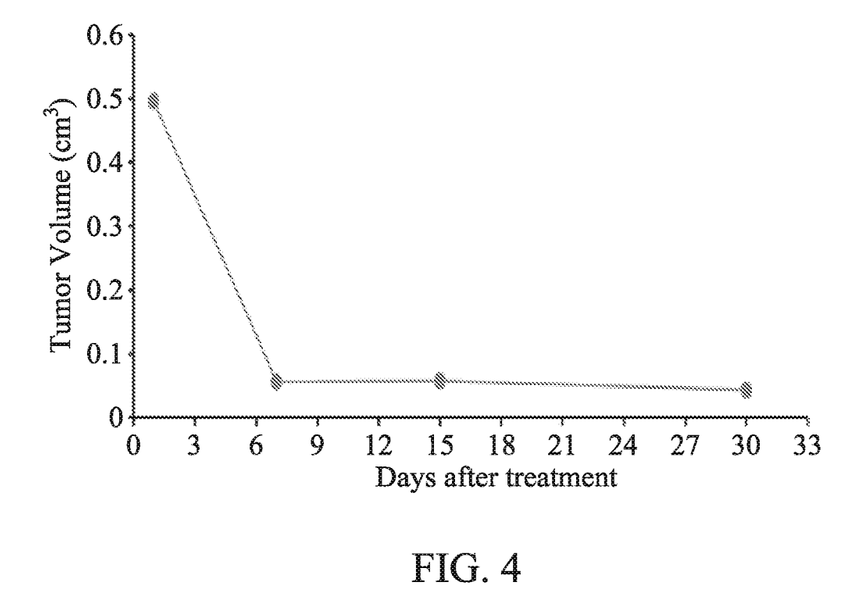
FIG. 4 shows the volume change of melanoma in the lesion of the cat (Case No. $C_{01}$-S01-E01) treated with the GWM100 drug.

The tumor volume of the lesion was 0.4953 cm$^3$ before the treatment (Day 1), and the tumor volume thereof was reduced to 0.043 cm$^3$ after the fourth administration (Day 30) (referring to FIG. 4). The biochemical examination of serum showed that the value of liver function of the cat fell within the reference values, and the renal function thereof was also stable.

Therefore, administration of the GWM100 drug of the present disclosure could effectively reduce the tumor volume of digital melanoma in cats.

Adverse Effects

No common side effects such as pain, nausea, vomiting or local redness and inflammation had been observed. The functions of liver and kidney were stable and normal during and after the treatment.

CONCLUSION OF THIS EMBODIMENT

The pharmaceutical composition of the present disclosure can effectively treat melanoma in dogs and cats by promoting the ablation of melanoma thereof, thereby improving the quality of life and clinical symptoms of dogs and cats suffering from melanoma. Furthermore, no significant increase in adverse reactions has been observed in the clinical trials.

The disclosure has been described using exemplary embodiments. However, it is to be understood that the scope of the disclosure is not limited to the disclosed embodiments. On the contrary, it is intended to cover various modifications and similar rearrangement. The scope of the claims therefore should be accorded the broadest interpretation so as to encompass all such modifications and similar arrangements.

What is claimed is:

1. A method for treating melanoma, comprising administering a therapeutically effective amount of a pharmaceutical composition to a subject in need thereof, wherein the pharmaceutical composition comprises a benzenesulfonamide derivative and a pharmaceutically acceptable carrier thereof, wherein the benzenesulfonamide derivative is represented by formula (I) below:

or a pharmaceutically acceptable salt thereof,
wherein $R_1$ to $R_7$ are independently selected from the group consisting of H, a $C_1$-$C_6$ linear or branched alkyl group, a $C_1$-$C_6$ linear or branched alkoxy group, a $C_3$-$C_6$ cycloalkyl group, a $C_3$-$C_6$ cycloheteroalkyl group, an amino group, and a halo group, or $R_6$ and $R_7$ are linked to each other to form a ring, and
wherein the alkyl, alkoxy, cycloalkyl, cycloheteroalkyl groups and the ring in $R_1$ to $R_7$ are independently unsubstituted or substituted with one or more substituents.

2. The method of claim 1, wherein the melanoma is non-UV-induced melanoma.

3. The method of claim 2, wherein the non-UV-induced melanoma is selected from the group consisting of mucosal melanoma, acral melanoma, ocular melanoma, non-UV-induced cutaneous melanoma, and any combination thereof.

4. The method of claim 3, wherein the subject is a human.

5. The method of claim 4, wherein the ocular melanoma is uveal melanoma.

6. The method of claim 3, wherein the subject is a dog or a cat.

7. The method of claim 6, wherein the mucosal melanoma is oral mucosal melanoma, and wherein the acral melanoma is digital melanoma.

8. The method of claim 1, wherein the substituent is selected from the group consisting of phenyl, halo, oxo, ether, hydroxyl, carboxyl, amino, sulfo and sulfonamide group.

9. The method of claim 1, wherein the benezesulfonamide derivative or the pharmaceutically acceptable salt thereof is at least one selected from the group consisting of para-toluene sulfonamide, ortho-toluene sulfonamide, meta-toluene sulfonamide, N-ethyl-ortho-toluene sulfonamide, N-ethyl-para-toluene sulfonamide, N-cyclohexyl-para-toluene sulfonamide, -continued -continued

10. The method of claim 1, wherein the pharmaceutically acceptable carrier is selected from the group consisting of a filler, a binder, a preservative, a disintegrating agent, a lubricant, a suspending agent, a wetting agent, a flavoring agent, a thickening agent, an acid, a biocompatible solvent, a surfactant, a complexation agent, and any combination thereof.

11. The method of claim 1, wherein the pharmaceutically acceptable carrier is selected from the group consisting of polyethylene glycol, alkylene glycol, propylene glycol, sebacic acid, dimethyl sulfoxide, ethanol, and any combination thereof.

12. The method of claim 1, wherein the pharmaceutical composition further comprises at least one of 10% to 40% by weight of polyethylene glycol-400, 5% to 10% by weight of propylene glycol, 1% to 5% by weight of sebacic acid, 0% to 15% by weight of p-toluenesulfonic acid, 10% to 20% by weight of 2-ethyl-1,3-hexanediol, 0% to 10% by weight of dimethyl sulfoxide, and 0% to 20% by weight of anhydrous ethanol.

13. The method of claim 1, wherein the benzenesulfonamide derivative is present in an amount of from 1% to 60% by weight.

14. The method of claim 13, wherein the benzenesulfonamide derivative is present in an amount of from 20% to 40% by weight.

15. The method of claim 1, wherein the pharmaceutical composition is in a form selected from the group consisting of a formulation for injection, dry powder, a tablet, an oral liquid, a wafer, a film, a lozenge, a capsule, a granule, a pill, a gel, a lotion, an ointment, an emulsifier, a paste, a cream, an eye drop, and a salve.

16. The method of claim 1, wherein the pharmaceutical composition is administered to the subject intratumorally, intravenously, subcutaneously, intradermally, orally, intrathecally, intraperitoneally, intranasally, intramuscularly, intrapleuraly, topically, or through nebulization.

17. The method of claim 1, wherein the pharmaceutical composition causes ablation of the melanoma.

18. The method of claim 1, wherein the benzenesulfonamide derivative in the pharmaceutical composition is administered to the subject in an effective amount of from about 3,300 mg to about 26,400 mg.

19. The method of claim 1, wherein the benzenesulfonamide derivative in the pharmaceutical composition is administered to the subject in an effective amount of from about 165 mg to about 6,600 mg per day.

* * * * *